(12) United States Patent
Ni

(10) Patent No.: US 6,382,510 B1
(45) Date of Patent: May 7, 2002

(54) AUTOMATIC INSPECTION SYSTEM USING BARCODE LOCALIZATION AND METHOD THEREOF

(75) Inventor: Catherine Wei-fen Ni, Hsinchu (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 09/490,314

(22) Filed: Jan. 24, 2000

(30) Foreign Application Priority Data

Feb. 2, 1999 (TW) .......................................... 88101584

(51) Int. Cl.$^7$ ................................................ G06K 5/04
(52) U.S. Cl. ........................... 235/462.08; 235/462.08; 235/462.05; 235/462.09; 235/462.1
(58) Field of Search ....................... 235/462.05, 462.08, 235/462.09, 462.1

(56) References Cited

U.S. PATENT DOCUMENTS

| | | | |
|---|---|---|---|
| 4,589,140 A | 5/1986 | Bishop et al. ................... 382/8 |
| 4,641,356 A | 2/1987 | Sternberg ..................... 382/49 |
| 4,809,308 A | 2/1989 | Adams et al. ................. 378/99 |
| 4,850,027 A | 7/1989 | Kimmel ........................ 382/49 |
| 5,017,795 A | 5/1991 | Dower et al. ................ 250/560 |
| 5,023,917 A | 6/1991 | Bose et al. ..................... 382/8 |
| 5,120,940 A | * 6/1992 | Willsie ........................ 235/462 |
| 5,465,308 A | 11/1995 | Hutcheson et al. .......... 382/159 |
| 5,495,537 A | 2/1996 | Bedrosian et al. .......... 382/209 |
| 5,546,475 A | * 8/1996 | Bolle et al. .................. 382/190 |
| 5,675,663 A | 10/1997 | Koerner et al. ............. 382/181 |
| 5,727,080 A | 3/1998 | Cox et al. .................... 382/168 |
| 6,073,849 A | * 6/2000 | Colley et al. ........... 235/462.27 |
| 6,206,287 B1 | * 3/2001 | Wasula et al. ......... 235/462.05 |
| 6,228,289 B1 | * 5/2001 | Powers et al. ............. 264/1.36 |

FOREIGN PATENT DOCUMENTS

| WO | WO-9706501 | * 8/1996 |
|---|---|---|

\* cited by examiner

Primary Examiner—Michael G. Lee
Assistant Examiner—Daniel Walsh
(74) Attorney, Agent, or Firm—Beyer Weaver & Thomas, LLP

(57) ABSTRACT

An automatic inspection system using barcode locator and the method thereof which can inspect a colored surface of a three-dimensional object having a barcode. The automatic inspection systems comprises a light source; an image-retrieving device; and an operating and processing device. The image-retrieving device retrieves three-dimensional images of the inspected object from various viewing angles. The three-dimensional images are converted into two-dimensional images, which are then connected to produce a two-dimensional image representing the inspected object by the operating and processing device. The two-dimensional image representing the inspected object is adjusted through the barcode locator. Thereafter, the two-dimensional image is compared with a reference object image previously stored by the operating and processing device to find the defined pre-defects of the inspected object. The automatic inspection system and inspecting method can provide high-speed inspection with a high accuracy for on-line production.

10 Claims, 7 Drawing Sheets

AUTOMATIC INSPECTION SYSTEM USING BARCODE LOCALIZATION AND METHOD THEREOF

BACKGROUND OF THE INVENTION

1. Field of the Invention

This invention relates to a machine visual apparatus, and more particularly to an automatic inspection system using barcode locator and a method thereof.

2. Description of Prior Art

Nowadays, machine vision has been widely adopted in the automatic inspection field, by which cameras and computers, instead of the human vision, are used to perform estimation and inspection, etc. It is accurate, reproducible and high-speed. Using machine vision for automatic inspection can reduce the cost and improve the quality of the products.

A typical application of machine vision is the inspection of PC boards, which is an operation of one-dimensional inspection for a two dimensional plane. Many high-speed inspections are needed while estimating the size of inductance and the intactness of the circuit. Machine vision can provide a high accuracy and reliability that is difficult to achieve by human inspection.

In U.S. Pat. No. 5,546,475, Bolle et al. disclose a produce recognition system which uses the histogram technique as the basis of segmenting and feature extraction. In U.S. Pat. No. 5,465,308, the input image is recognized through spectrum analysis and neural networks.

The above prior arts have to perform a large number of correlation operations. That is, an excellent processing speed must be provided; otherwise, it will take a long time to perform the operation. Therefore, U.S. Pat. No. 5,495,537, "Methods and apparatus for machine vision template matching of image predominantly having generally diagonal and elongate features", introduces the operations of hill climbing and segment peak finding into the 4-way or 8-way search system to reduce the number of correlation operation.

When recognizing an object, the brightness distribution on the surface of the object has a significant effect on the recognition result. To avoid the difficulty of object recognition at different viewing angles due to various illuminations, U.S. Pat. No. 57,227,080 discloses a technique similar to the dynamic time warping method to perform dynamic histogram warping of the image histograms, thereby achieving constant image brightness for stereo pair images.

A typical on-line application of machine vision uses the edge detection technique to enhance the characteristics and performs several certain measurements to filter out defective products. Basically, it is a one-dimensional detection technique, which is not suitable for two-dimensional inspection of the surface of a three-dimensional object.

The current inspection techniques for three-dimensional objects, such as aluminum cans, is not accurate enough for the product line. Furthermore, it cannot proofread a whole two-dimensional surface.

SUMMARY OF THE INVENTION

Accordingly, to overcome the drawbacks of the prior arts, the object of this invention is to provide an automatic inspection system using barcode locator and a picture-content proofreading technique, which can provide a high-speed, high accuracy inspection for a three-dimensional object.

The automatic inspection system of this invention has two features: First, it is a three-dimensional inspection system. Taking the inspection of an aluminum can as an example, the on-line three-dimensional inspection is accomplished with uncertain view angles. Second, it provides the ability to rapidly switch the type of objects inspected. That is, the inspection system can inspect a variety of different cans if their outlines are similar to each other.

For the automatic inspection of aluminum cans, the direction of aluminum can is not pre-determined when the image of the aluminum is retrieved on the production line. Thus, the reference point has to be located before comparison. Nowadays, every aluminum can is provided with a barcode, which has a significant area and is easy to recognize. Therefore, the barcode is used as a reference position in this invention.

To achieve the above object, this invention provides an automatic inspection system using barcode locator to inspect a colored surface of a three-dimensional object having a barcode. The automatic inspection system comprises: a light source for uniformly illuminating the three-dimensional object; an image retrieving device for retrieving and analyzing images of the object from various viewing angles; an operating and processing device for receiving data of three-dimensional images output from the image retrieving device, segmenting the three-dimensional images, converting the three-dimensional images into two-dimensional images, then connecting the two-dimensional images of various viewing angles to obtain an image representing the three-dimensional object, and comparing the two-dimensional image with a reference object image previously stored in the operating and processing device to find defects of the inspected object.

BRIEF DESCRIPTION OF THE DRAWINGS

The following detailed description, given by way of example and not intended to limit the invention solely to the embodiments described herein, will best be understood in conjunction with the accompanying drawings in which.

DETAILED DESCRIPTION OF THE PREFERRED EMBODIMENTS

Figure 1:
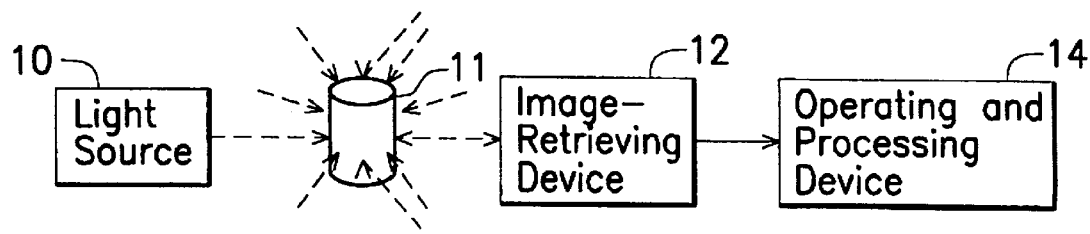
FIG. 1 is a block diagram illustrating the automatic inspection system using barcode locator of this invention.

Referring to FIG. 1, according to this invention, the automatic inspection system using barcode locator comprises: a light source 10 for providing an uniform illumination on the surface of an inspected object 11, such as an aluminum can; an image retrieving device 12, which includes a plurality of cameras, for retrieving three-dimensional images of the inspected object, which is uniformly illuminated by the light source 10, from various viewing angles; an operating and processing device 14 for receiving the three-dimensional images input from the image retrieving device 12, then converting the three-dimensional images into two-dimensional images, and connecting the two-dimensional images to produce a two-dimensional image representing the inspected object, adjusting the two-dimensional image based on the position of the barcode, and then comparing the two-dimensional image representing the inspected object Th a reference object image previously stored in the operating and processing device to find the defined defects of the inspected object.

Since the inspected object is cylindrical, the light source 10 can be a ring-type light tube or special designed LEDs. Furthermore, two light tubes can be used to provide a uniform illumination on the surface of the inspected object at the top and the bottom of the inspected object, respectively.

The image-retrieving device 12 includes a plurality of cameras and a frame grabber. The camera can be a CCD (charge-coupled device) camera. In this embodiment, three CCD cameras, which are equally spaced apart around the inspected object, are used to retrieve the images of the inspected object from various viewing angles, so as to obtain the images for the whole cylindrical surface of the inspected object.

In this embodiment, the operating and processing device is a computer for performing the image processing and comparing operation.

Figure 2:
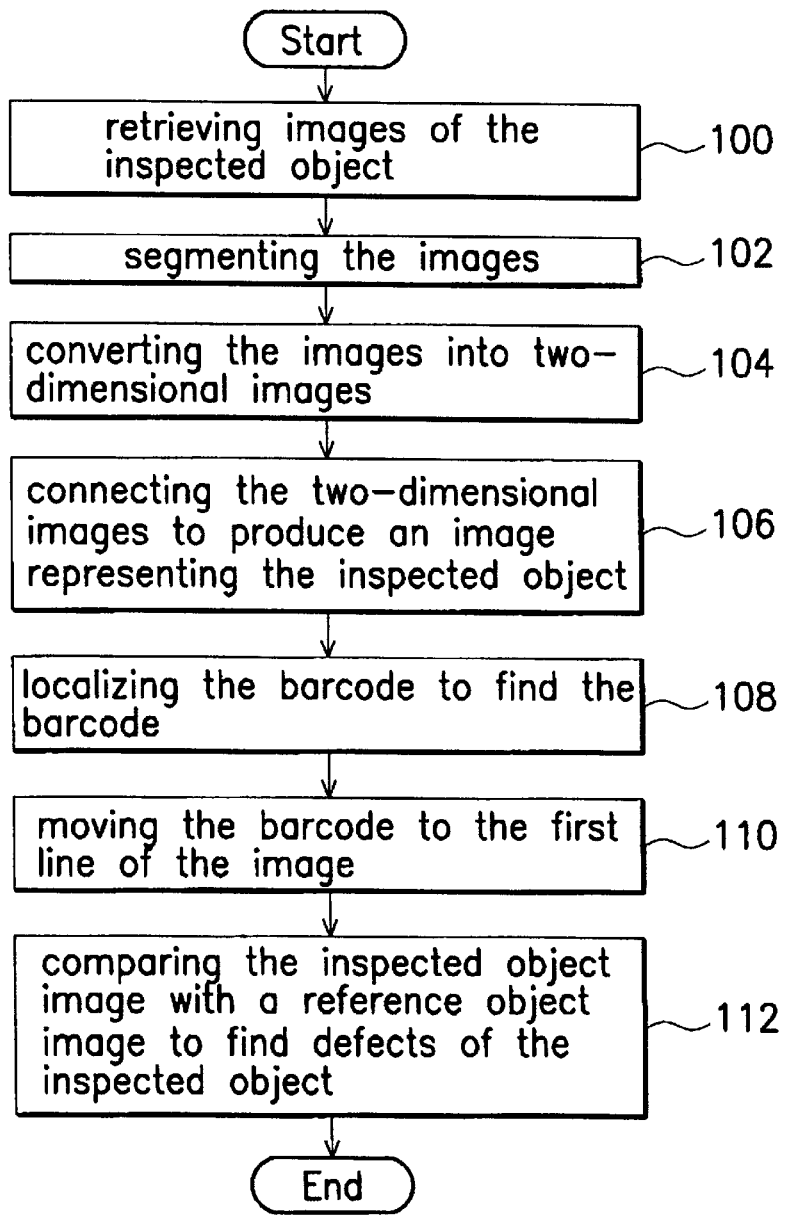
FIG. 2 is a flow chart illustrating the automatic inspecting method of this invention.
Figure 3A:
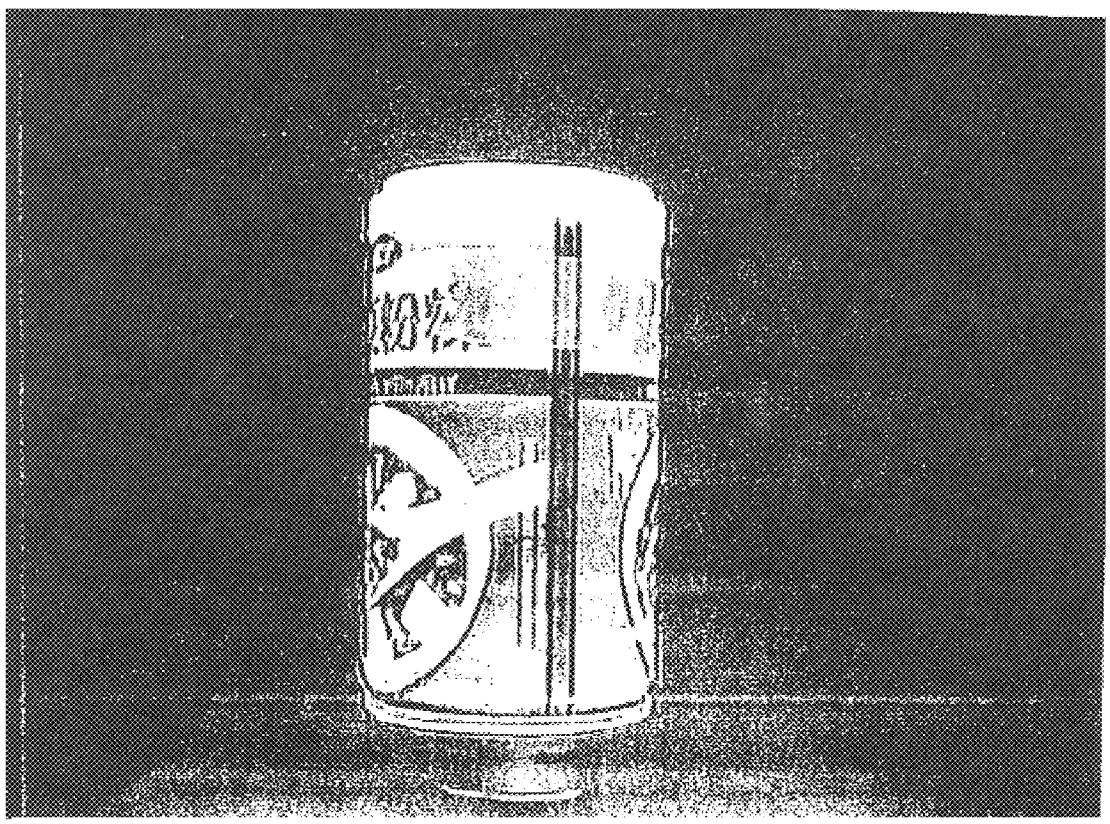
FIGS. 3a to 3f are copies of photographs illustrating the inspecting process according to the automatic inspecting method of this invention.
Figure 3B:
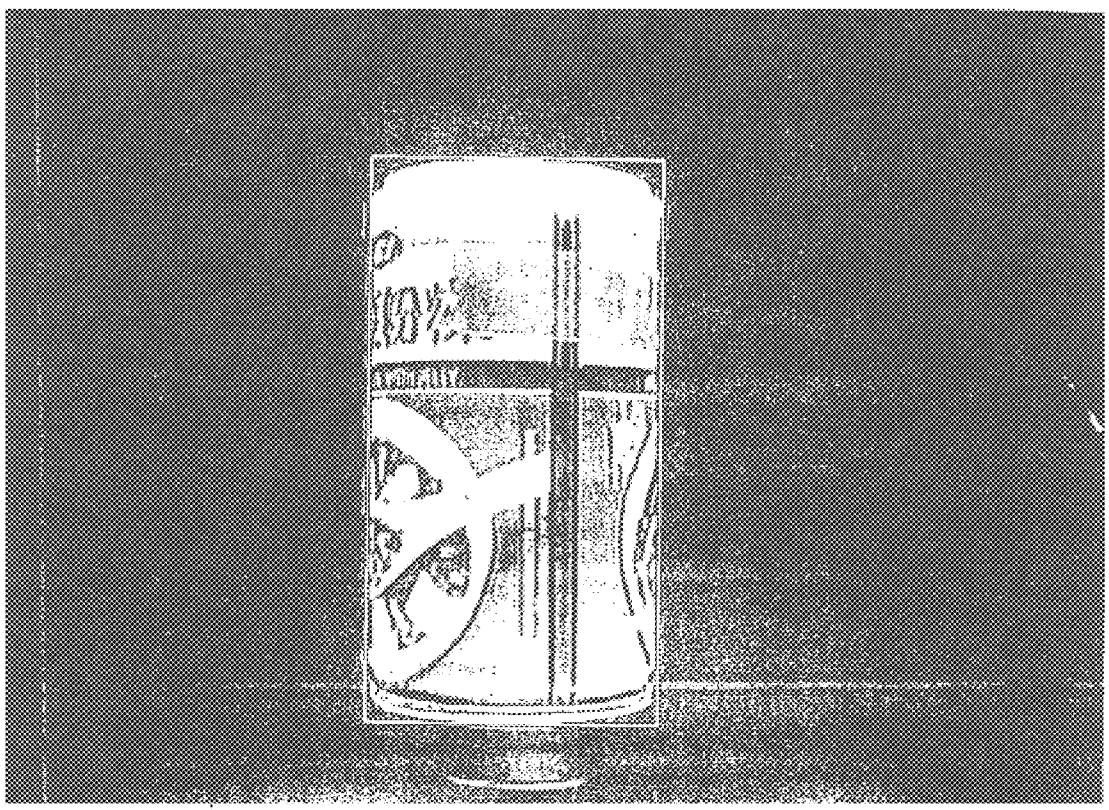
Figure 3C:
Figure 3D:
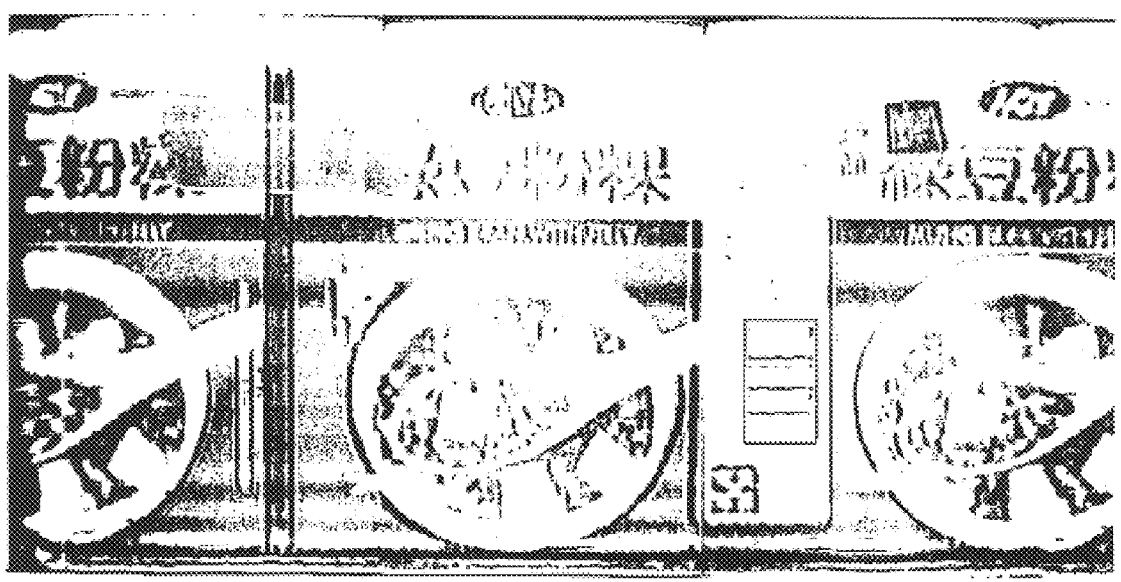
Figure 3E:
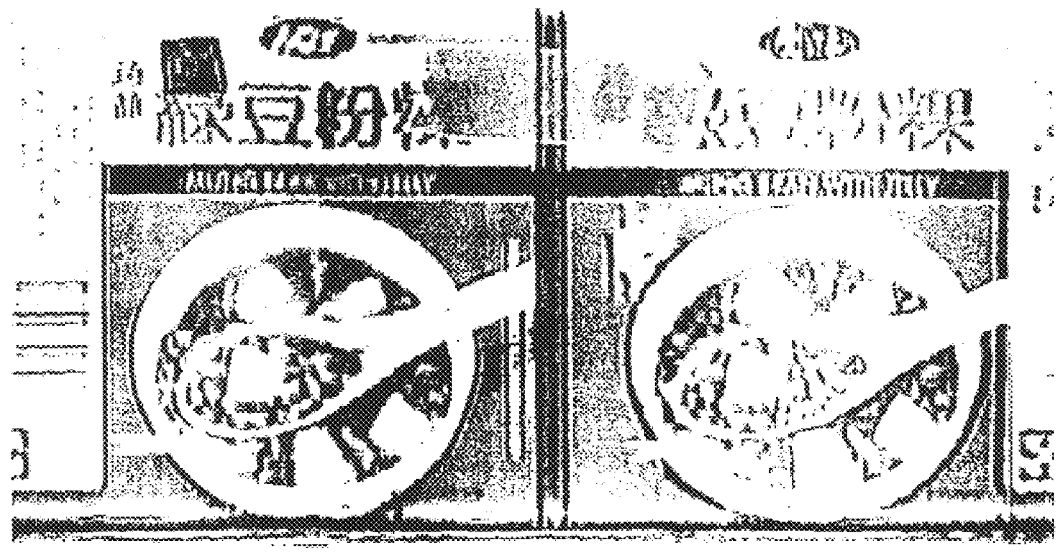
Figure 3F:
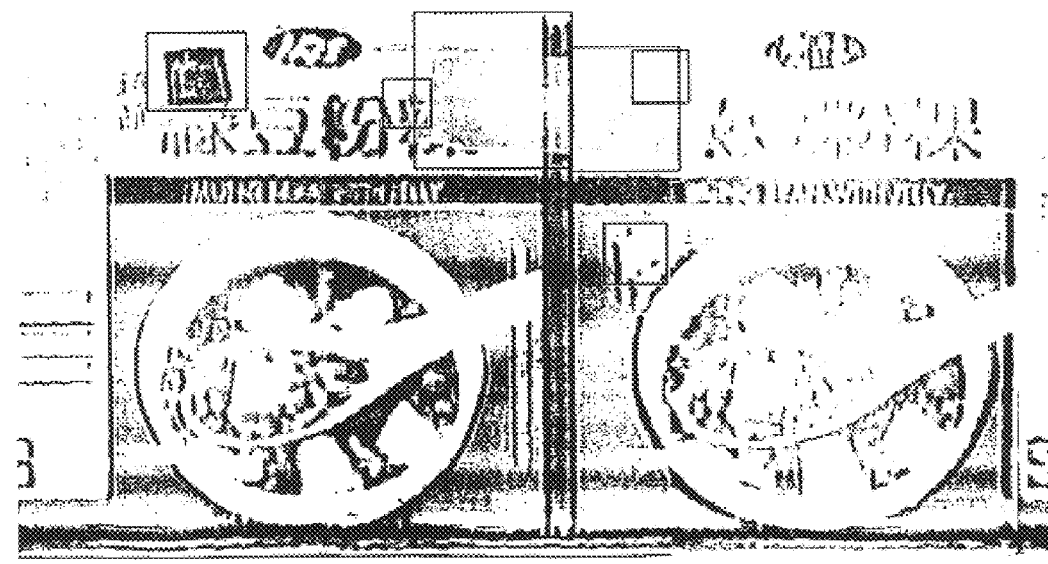
Figure 4A:
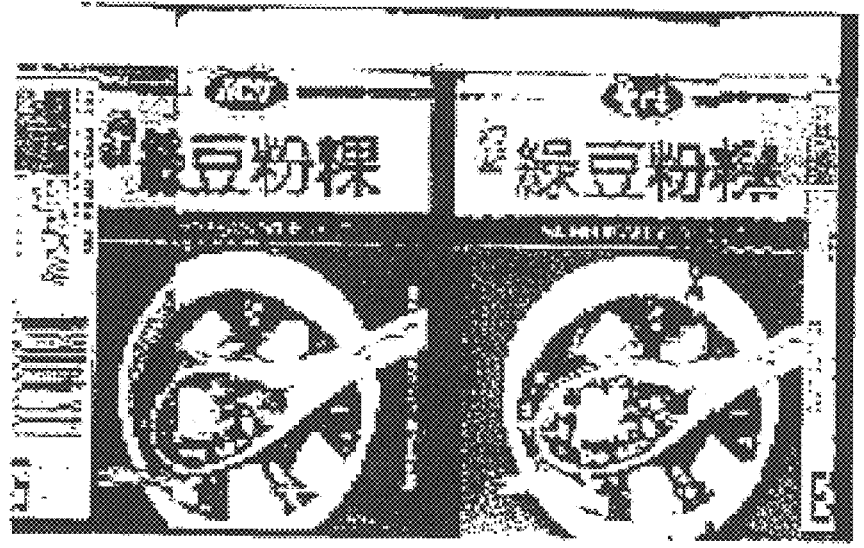
FIGS. 4a to 4d are copies of photographs illustrating the comparing process in the automatic inspecting method of this invention.
Figure 4B:
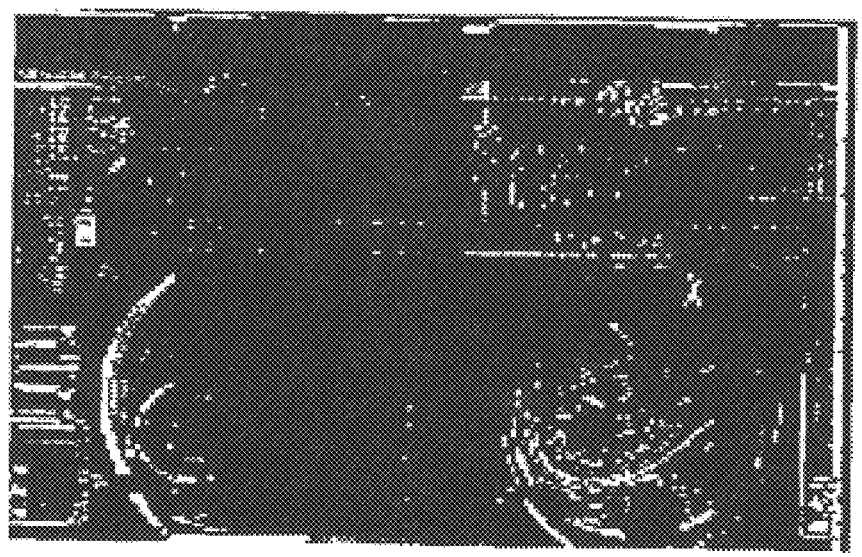
Figure 4C:
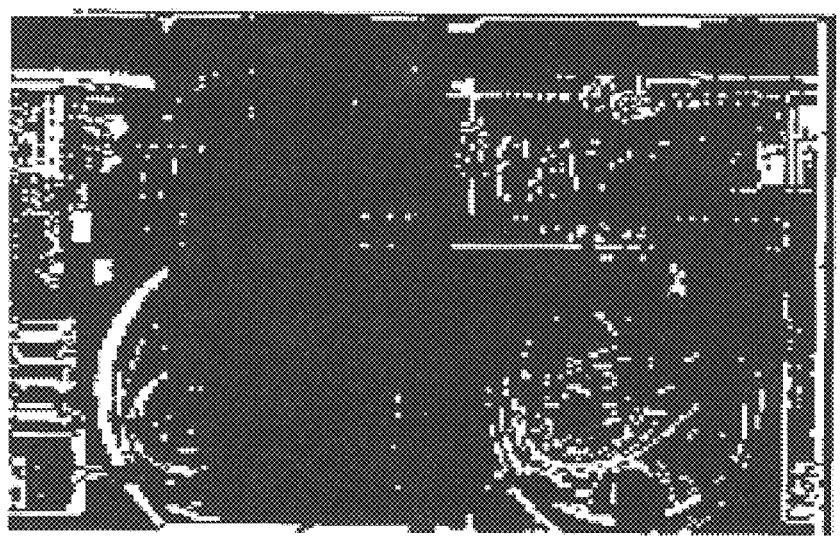
Figure 4D:
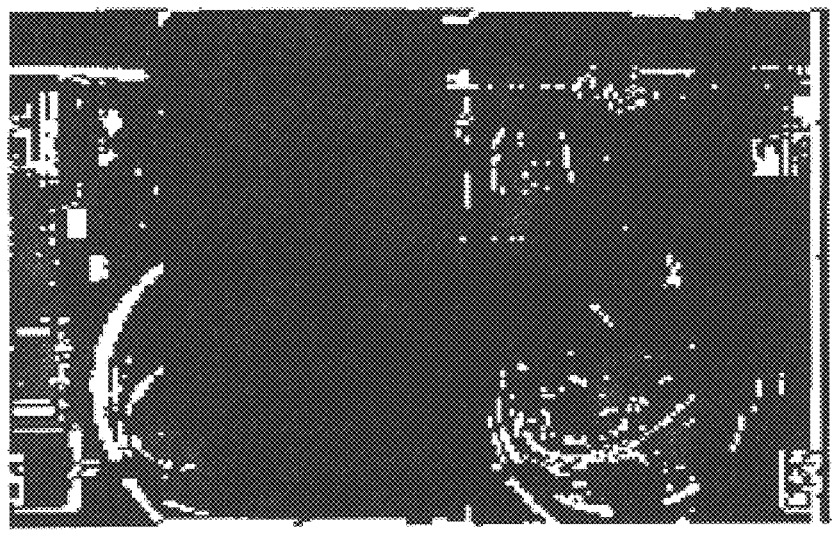

Referring to FIG. 2, the operating process of the automatic inspection system of this invention comprises the steps of: (i) step 100, referring to FIG. 3a, retrieving three-dimensional images of the inspected object by the image retrieving device; (ii) step 102, referring to FIG. 3b, segmenting the retrieved three-dimensional images; (iii) step 104, referring to FIG. 3c, converting the three-dimensional images into two-dimensional images by the operating and processing device; (iv) step 106, referring to FIG. 3d, connecting the two-dimensional images to produce a two-dimensional image representing the inspected object; (v) step 108, locating the barcode to find the barcode on the two-dimensional image representing the inspected object; (vi) step 110, referring to FIG. 3e, adjusting the two-dimensional image to move the barcode to the first line of the image; (vii) step 112, referring to FIG. 3f, comparing the two-dimensional image representing the inspected object with a reference object image previously stored in the operating and processing device to find the pre-defined defects of the inspected object.

In the above process, the using of barcode locator provides on-line production inspection with the ability to rapidly switch the type of object inspected. Furthermore, based on the unidirectional feature of a barcode, a barcode can be quickly found by edge detection and one-way erosion/dilation operations.

Referring to FIGS. 4a to 4d, the comparing process comprises the steps of: (i) referring to FIG. 4a, performing a correlation operation for best alignment of the inspected object image to the reference object image; (ii) referring to FIG. 4b, obtaining a residual image of the obtained image and the stored image, and performing histogram equalization; (iii) producing binary pixel-values, referring to FIG. 4c, and performing image-negative transforming and closing operations to clean up the residual noises; and (iv) referring to FIG. 4d, deciding whether the residual image contains pre-defined defects.

The definition of a defect can be changed according to practical requirements of the object for automatic inspection.

While the present invention has been particularly shown and described with reference to a preferred embodiment, it will be readily appreciated by those of ordinary skill in the art that various changes and modifications may be made without departing from the spirit and scope of the invention.

It is intended that the claims be interpreted to cover the disclosed embodiment, those alternatives which have been discussed above and all equivalents thereto.

What is claimed is:

1. An automatic inspection system using barcode locator, which can inspect a colored surface of a first three-dimensional object having a barcode, comprising:

a light source for uniformly illuminating the first three-dimensional object;

an image-retrieving device for retrieving and analyzing three-dimensional images of the first object at various viewing angles;

an operating and processing device for receiving three-dimensional images from the image retrieving device, segmenting the three-dimensional images, converting the three-dimensional images into two-dimensional images, connecting the two-dimensional images of various viewing angles to obtain a single two-dimensional image representing the first three-dimensional object, using a barcode in the single two-dimensional image to position the single two-dimensional image in a first predefined position and comparing the two-dimensional image with a reference object image previously stored in the operating and processing computer to find defects in the colored surface of the first three-dimensional object.

2. An automatic inspection system as claimed in claim 1 wherein the operating and processing device is a computer that performs the following operations: a segmenting process for finding the object in an image; a converting process for connecting the images of various viewing angles to obtain a two-dimensional image representing the inspected object; an orientation process using a barcode in the single two-dimensional image to position the single two-dimensional image in a first predefined position; and a comparing process for comparing the two-dimensional image representing the inspected object with a previously stored reference object image to find defects of the inspected object.

3. An automatic inspection system as claimed in claim 1 wherein the light source is an illuminating system that can provide an uniform illumination for a surface of the object.

4. An automatic inspection system as claimed in claim 1 wherein the image-retrieving device comprises a plurality of CCD cameras and a frame grabber.

5. An automatic inspection system as claimed in claim 1 wherein the comparing process comprises the steps of (1) performing a correlation operation for best alignment of the inspected object image to the reference object image; (ii) obtaining a residual image of the obtained image and the stored image; (iii) producing binary pixel-values and performing image-negative transforming and closing operations for the residual image; and (iv) deciding whether the residual image contains pre-defined defects.

6. An automatic inspection system as claimed in claim 4 wherein the light source includes one of two ring-type light tubes and LEDs.

7. An automatic inspection system as claimed in claim 4 wherein the image-retrieving device includes at least three CCD cameras.

8. An automatic inspection method using barcode locator, for inspecting a colored surface of a first three-dimensional object having a barcode, comprising the steps of:

(i) retrieving three-dimensional images of the first three-dimensional object by an image retrieving device, and segmenting the three-dimensional images;

(ii) converting the three-dimensional images into two-dimensional images by an operating and processing computer;

(iii) connecting the two-dimensional images of various viewing angles to obtain a two-dimensional image representing the first three-dimensional object;

(iv) locating the barcode in the two-dimensional image;

(v) adjusting the position of the two-dimensional image so that the barcode is positioned in a first predefined position;

(vi) comparing the positioned two-dimensional image of the first three-dimensional object with a reference object image previously stored in the operating and processing computer to find pre-defined defects in the first three-dimensional object.

9. An automatic inspecting method as claimed in claim 8 wherein, in step (iv), the barcode is located by using edge detection and one-way erosion/dilation operations.

10. An automatic inspecting method as claimed in claim 8 wherein the comparing process of step (vi) comprises the steps of (1) performing a correlation operation for obtaining a best, alignment of the first three-dimensional object image to the reference object image; (2) obtaining a residual image of the obtained image and the stored image; (3) producing binary pixel-values and performing image-negative transforming and closing operations for the residual image; and (4) deciding whether the residual image contains pre-defined defects.

* * * * *